United States Patent [19]
Long et al.

[11] Patent Number: 6,038,931
[45] Date of Patent: Mar. 21, 2000

[54] METHOD AND APPARATUS FOR THE TESTING OF PLASTICALLY DEFORMABLE OBJECTS

[75] Inventors: David C. Long, Wappingers Falls; Thomas P. Moyer, Lagrangeville; Keith C. O'Neil, Hughsonville; Charles H. Perry, Poughkeepsie; Glenn A. Pomerantz, Kerhonkson, all of N.Y.; James R. Case, Brackney, Pa.; Laszlo Kando, Hopewell Junction; John E. Kozol, Binghamton, both of N.Y.

[73] Assignee: International Business Machines Corporation, Armonk, N.Y.

[21] Appl. No.: 09/025,672

[22] Filed: Feb. 18, 1998

Related U.S. Application Data

[60] Provisional application No. 60/058,627, Sep. 11, 1997.

[51] Int. Cl.[7] ...................................................... G01N 3/20
[52] U.S. Cl. .................................. 73/850; 73/849; 73/851
[58] Field of Search ............................. 73/760, 783, 788, 73/800, 812, 849, 851, 835, 834, 838, 850

[56] References Cited

U.S. PATENT DOCUMENTS

| | | | |
|---|---|---|---|
| 2,469,346 | 5/1949 | Watter | 73/812 |
| 3,274,825 | 9/1966 | Wahlgren | 73/812 |
| 3,831,483 | 8/1974 | Schmidt | 73/852 |
| 4,358,962 | 11/1982 | Ashby et al. | 73/849 |

*Primary Examiner*—Max Noori
*Attorney, Agent, or Firm*—Tiffany L. Townsend

[57] ABSTRACT

A method for testing the integrity at least two test objects, each object is made of a plastically deformable material, by a. contacting a moving means with the objects at a first point in time, the moving means at a first position and the objects at a first position, the moving means having a shaped portion; b. shifting at least a portion of the objects to a second position at a second time, subsequent to the first time, wherein at least a portion of the objects were displaced during the interval between the first time and the second time; c. evaluating the objects after the shifting in step b. 22.

37 Claims, 7 Drawing Sheets

METHOD AND APPARATUS FOR THE TESTING OF PLASTICALLY DEFORMABLE OBJECTS

CROSS-REFERENCE TO RELATED APPLICATIONS

The present application claims priority to co-pending U.S. provisional application Ser. No. 60/058,627 filed Sep. 11, 1997.

FIELD OF THE INVENTION

This invention is concerned with pre-completion destructive testing of plastically deformable materials. More particularly, this invention relates to the testing of the durability of more than one C4 or other solder connection joint during one testing interval.

BACKGROUND OF THE INVENTION

The use of materials comprising plastically deformable materials has increased in a number of industries. Solder balls are an example of an object comprising a plastically deformable material. The use of solder balls is wide-spread in the microelectronic packaging industry. The testing of solder ball assemblies in microelectronic packages is well known in the industry. Various techniques exist which test the strength and fitness of solder ball assemblies. Some methods involve in-line testing and others are after process testing methods. Most in-process methods are destructive, the in-line methods also tend to be slower in that one solder ball assembly at a time is tested. Current testing methods involve testing the force required to "lift" or shear a solder ball from its original location, such that the entire solder ball assembly is relocated. While it is possible to test more than one solder ball assembly at one time, since an accurate calculation of the force necessary to move each individual solder ball is difficult to determine when more than one is moved at a time it would be advantageous to explore the possibility of other testing techniques.

Other methods of testing the fitness of solder ball assemblies involve testing the assemblies after processing is complete. The after process methods can be both destructive and non-destructive. The after processing testing can be disadvantageous because large quantities of product can be produced before the non-conformity is identified. Additionally, in high production scenarios where product is shipped quickly, non-conforming product may already have been shipped before the non-conformity is discovered.

The time and resources needed to test solder ball assemblies increases as the complexities of the underlying packages increases. In the case of packages having grid arrays of solder ball assemblies, both ceramic and ball grid array packages, the amount of space between the solder balls decreases with each generation of packages and the complexity of the circuitry in the packages increases with each passing generation. The time and difficulty of in line testing each solder ball individually using current methods makes it difficult to further process the chips at the speed necessary to ensure that the packages can be produced using high speed processing techniques. Thus there remains a need for a method of testing solder ball assemblies where more than one solder ball assembly is tested during one testing interval. There also remains a need for a method of testing solder ball assemblies where the testing can occur in-line before large quantities of product are produced.

SUMMARY OF THE INVENTION

It is therefore an object of the present invention to provide a method for testing the integrity of more than one test object in a testing cycle.

It is another object of the present invention to provide an apparatus for testing the integrity of more than one test object in a testing cycle.

In accordance with the above listed and other objects, we invent a method for testing the integrity at least two test objects, each object comprising a plastically deformable material, comprising the steps of:

a. contacting a moving means with the objects at a first point in time, the moving means at a first position and the objects at a first position, the moving means having a shaped portion;

b. shifting at least a portion of the objects to a second position at a second time, subsequent to the first time, wherein at least a portion of the objects were displaced during the interval between the first time and the second time;

c. evaluating the objects after the shifting in step b. We also invent an apparatus for use with the method.

BRIEF DESCRIPTION OF THE DRAWINGS

These and other features, aspects and advantages will be more readily apparent and better understood from the following detailed description of the invention, in which.

DETAILED DESCRIPTION OF THE INVENTION

The present invention discloses a method and apparatus to test the operability of a plurality of test objects during one testing interval. Generally, the apparatus of the present invention, interacts with surfaces having a plurality of protrusions. Specifically, the primary embodiment of the apparatus interacts with a surface having a plurality of plastically deformable bodies. For the purposes of the present discussion, all of the protrusions will be referred to as plastically deformable bodies, unless it is indicted otherwise. Also, for the purposes of the present discussion, the surface having the plastically deformable body will comprise a ceramic, unless it is indicated otherwise. At least two of the plastically deformable bodies will be designated as test objects. It is not required that all of the plastically deformable bodies on a surface be test objects. The test objects are usually presented in a pattern. For example, the test objects could be presented so that rows of test objects are identifiable. However, it should be noted that a definite pattern need not exist for the current method to be operable. It is only necessary that more than one test object be tested during each test interval. In a preferred embodiment all of the plastically deformable bodies on a surface would be test bodies. Additionally, the plastically deformable bodies may comprise more than one material and comprise more than one portion. The plastically deformable body may be a solder ball having a ball limiting metallurgy in contact with the surface.

The apparatus of the present invention includes a moving means. The moving means contains a shaped object. The configuration of the shaped object should be such that it is capable of contacting each test object involved in an individual test interval.

Figure 1:
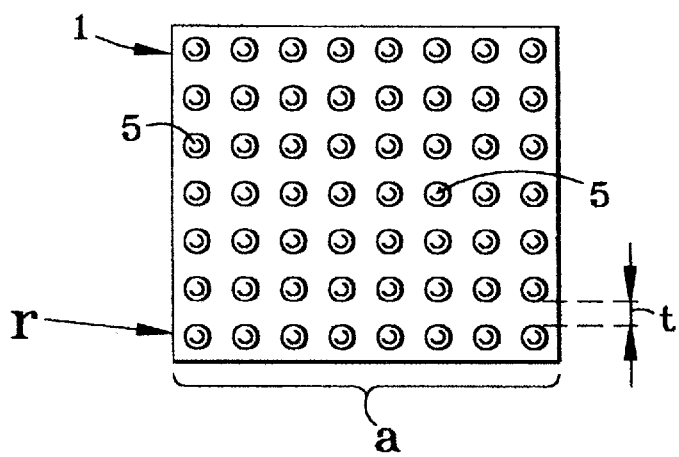
FIG. 1 is a top down view of the test objects being acted upon in the method and apparatus of the present invention.
Figure 2:
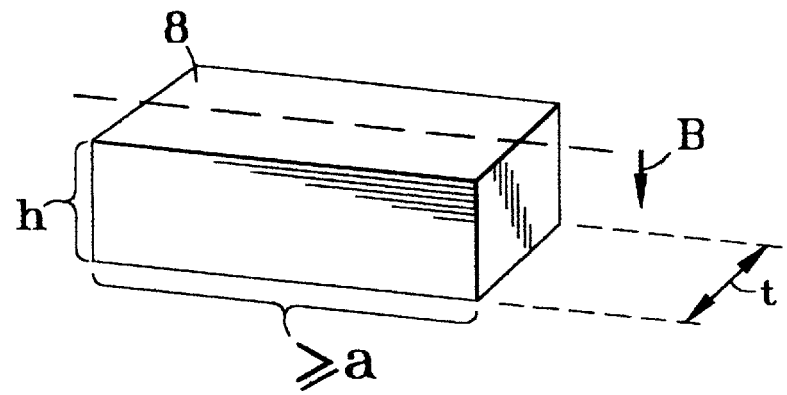
FIG. 2 is a view of one depiction of an element of the apparatus of the present invention.

An example of the present apparatus is given below. The surface, 1, containing the test objects, 5, would preferably be arranged in rows, r, of a predetermined length, a, as shown in FIG. 1. The test objects would be of substantially the same size and shape and preferably, the spacing between the rows, t, would be in a repeated pattern or a predetermined configuration. The shaped object, 8, of the moving means as shown in FIG. 2 would preferably be rectangular and the depth of the shaped object would be less than t, the distance between the rows of test objects. The height of the shaped object would be greater than the height of the test objects and the width of the shaped object would be at least about equal to a, the length of a row of test objects. The shaped object need not be rectangular, the only shape requirement is that the moving means not contact the test objects such that a significant pressure is exerted on the test objects prior to the movement during the testing interval. It is also preferable that the shaped object be placed at an adjustable fixed distance from the surface containing the test objects.

Figure 4:
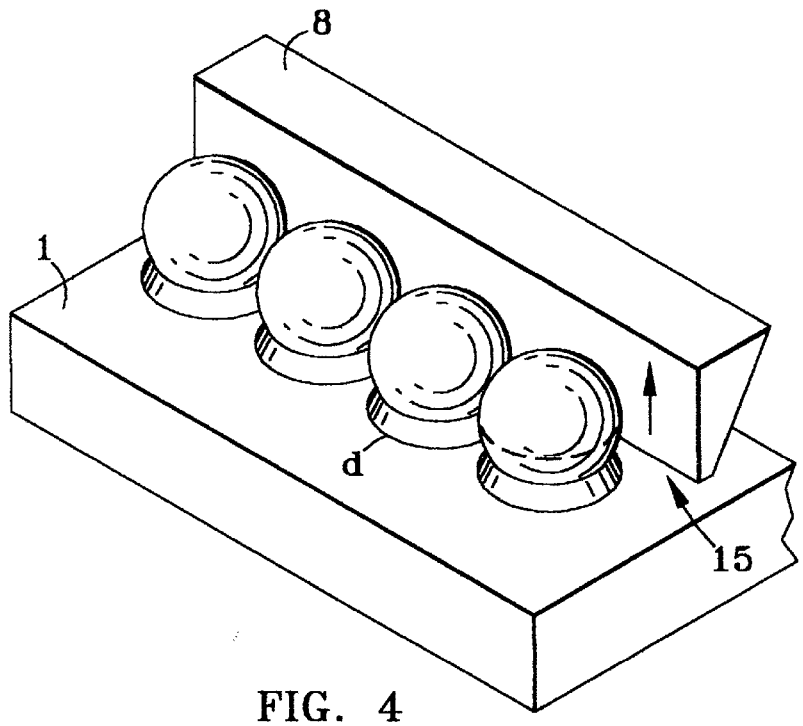
FIG. 4 is an isometric view of one step of the method of the present invention.
Figure 5:
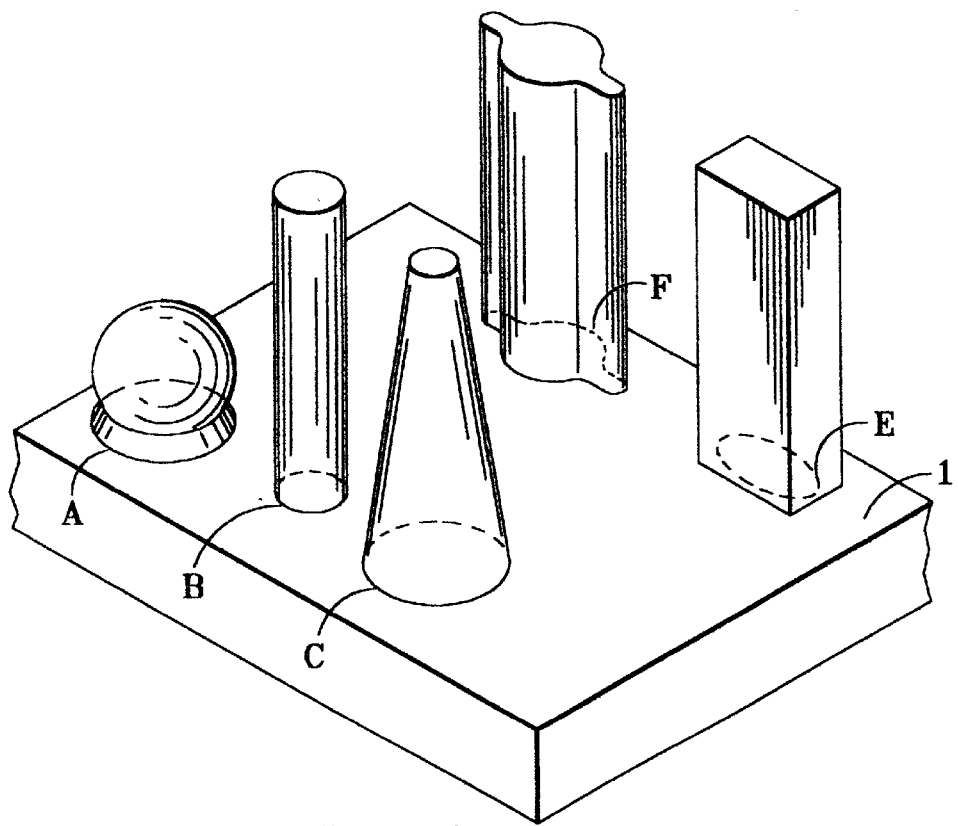
FIG. 5 is an isometric view of a variety of shapes of a diameter that may be encountered while practicing the method and apparatus of the present invention.

As shown in FIG. 4, prior to a test interval the moving means should be placed such that the distance between the surface, 1, and the lowest effective edge, 15, of the moving means, 8, is at least about 1% and at most about 50% of the diameter, d, of the test objects. The lowest effective edge, 15, of the moving means, 8, must be at least about 1% of the diameter so that the method of the invention does not provide data that corresponds to the torquing that would occur from a movement of the test object if the pressure is exerted at what is essentially the surface containing the test objects, sometimes referred to as peeling. By diameter it is meant the diameter of the test object where it contacts the surface containing the test objects. Examples of some, but not all, possible diameters are shown as A, B C, E and F in FIG. 5. Preferably, the height of the lowest effective edge is at least about 5% and at most about 30% of the diameter, d, of the test objects. By lowest effective edge it is meant that in a case where the shaped object of the moving means is not a rectangular shape, the lowest effective edge would be the edge corresponding to the plane defined by q, the side of the moving means, 8, which faces the test objects, as shown in FIG. 4. In a preferred embodiment, all of the plastically deformable bodies would be test objects and the moving means would be shaped so as to facilitate the testing of all of the test objects uniformly in one test interval. It should be noted that the apparatus and method of the present invention are not dependent on the shape of the test objects, the present method and apparatus are operable for any shape test object.

While it is preferred that the test objects be spherical or columnar, the present invention involves the use of the diameter of the test object where it connects to the surface containing the test objects. It is also preferred that the test objects be solder balls.

Figure 3:
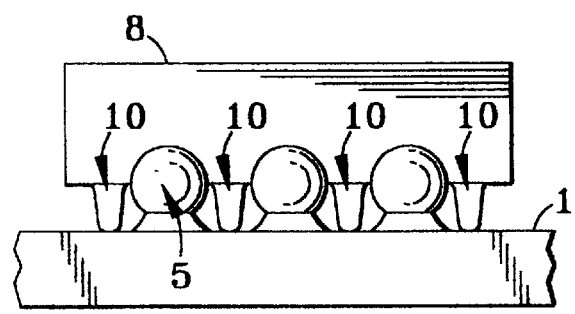
FIG. 3 is a front view of one embodiment of an element of the apparatus of the present invention.

The moving means may contain a distancing portion, 10, in operable communication with the shaped object as shown in FIG. 3. The distancing portion can be integral or separate from the shaped object. The distancing portion functions to position the shaped object such that the shaped object does not contact the surface containing the test objects. Preferably the shaped object does not contact the surface containing the test objects. In a preferred embodiment the distancing portion would be a protrusion, a wire or a similar mechanical means. In a more preferred embodiment, the distancing portion would not contact the test objects.

The method of testing defined in the present invention evaluates the operability of plastically deformable bodies. The method provides information regarding the failure of the plastically deformable bodies in the area surrounding connection point between the plastically deformable body and the underlying surface. Failures of different types of plastically deformable bodies, for example those attached to ceramic, organic and polymer surfaces or attached to metal pad on ceramic, organic and polymer surfaces might manifest in different manners. However, within a type of plastically deformable bodies, operable plastically deformable bodies will respond similarly. Deviations from an acceptable response of an operable plastically deformable body can be established and failures identified.

All further discussion and examples will presume that the surface containing the plastically deformable bodies is substantially parallel to the X axis. If the surface is not substantially parallel to the X axis the proper relationships will have to calculated based on the examples where the surface is parallel to the X axis. The method of the present invention is not dependent on the surface being parallel to the X axis. An operable plastically deformable body will react in a particular manner to the test. All plastically deformable bodies not reacting in the particular manner, while not necessarily defective, will be considered as being of a significant risk of being defective. A plastically deformable body in communication with a metallic interface on a ceramic surface will be used to illustrate the instant invention. An operable plastically deformable body, will relocate in the manner shown in A of FIG. 9, when the method of the instant invention is employed.

Figure 10A:
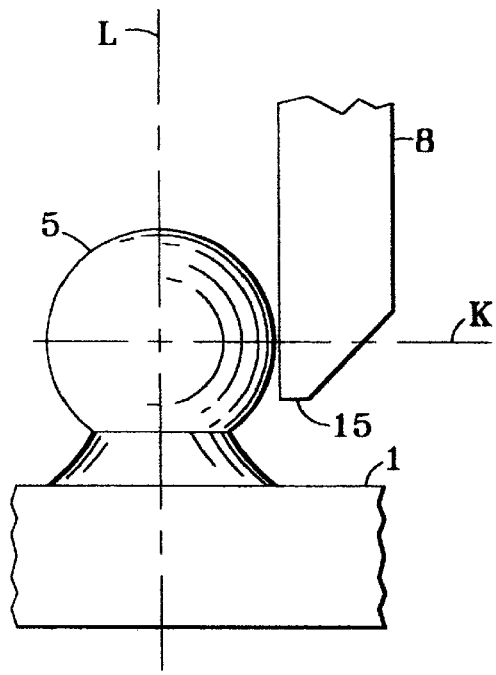
FIGS. 10a and 10b are another cross-sectional view of a method of the present invention.
Figure 10B:
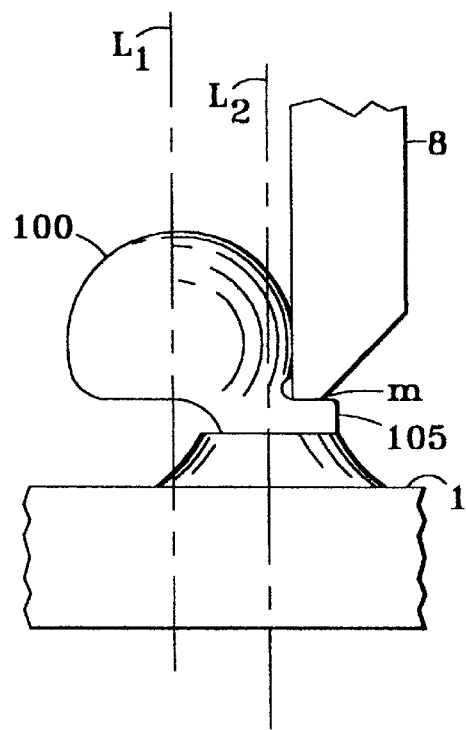

As shown in FIG. 10a, before the method of the present invention, the plastically deformable body has an axis, K, which, preferably, is the axis substantially parallel to the surface at a point of the largest diameter above the lowest effective edge, 15, of the moving means, 8. The plastically deformable body, 5, also has an axis, L, which is, preferably, the axis perpendicular to the surface at a point of the largest diameter above the lowest effective edge. A portion of the plastically deformable body, 5, on the surface, 1, is identifiable as an area of attachment, 3, between the plastically deformable body, 5, and the surface. In a preferred embodiment, the area of attachment, 3, of the plastically deformable body, 5, is below the lowest effective edge, 15, of the moving means, 8. After the testing interval, there will be two parts to each plastically deformable body, as shown in FIG. 10b. The upper portion, 100, has been shifted in relation to the lower portion, 105. The lower portion, 105, roughly conforms to the area of attachment, 3, in FIG. 10a. The upper portion has a first axis, L1, and the lower portion has a second different axis, L2. A plastically deformable body will have a lower portion, 105, where the lower portion has an exposed surface, M, substantially parallel to axis K. The exposed surface will be created by the interaction of the moving means and the surface containing the test objects. For example, an optimal reaction for an operable plastically deformable body comprising solder on a ceramic surface occurs when substantially all of the points on the exposed surface, M, contact any single plane parallel to axis K, when the parallel plane contacts at least one point on the surface. However, it should be noted that the response from a conforming plastically deformable body may be dependent on the combination of the type of body, the interface between the body and the surface, and the surface itself. The particular operator for any particular application and any combination of plastically deformable bodies and surfaces can determine at what point a deviation from the reaction constitutes a failure of the test.

Figure 10C:
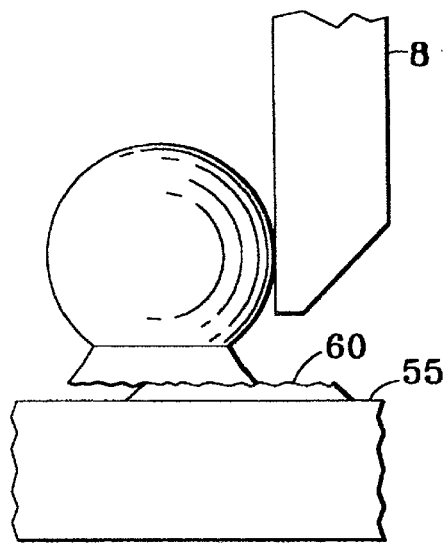
FIGS. 10c and 10d are yet another isometric view of a method of the present invention.
Figure 10D:
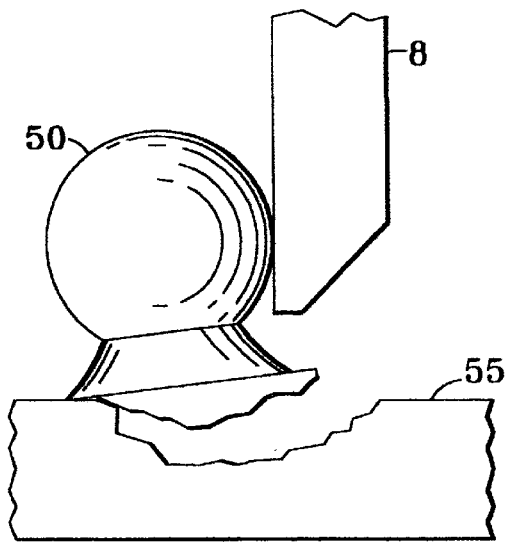

As another example, where a polymer comprising surface has a plastically deformable body attached, a difference between the response to the test method for an operable plastically deformable body and the reaction of a non-operable deformable body is generally observable. In the case of a plastic deformable body on a polymer surface, an optimal reaction is usually identifiable where the entire plastic deformable body, 50, is ripped from the surface, 55, containing the plastic deformable body, the plastic deformable body on a polymer remains as a single unit, as shown in FIG. 10d. An optimal reaction of a plastic deformable body on a polymer can be exemplified where the integrity of the interface is stronger than the cohesive strength of the polymer, and therefore the surface containing the plastic deformable bodies rips. A non-conforming reaction would be a reaction that is not substantially similar to that shown in FIG. 10d, for example the reaction shown in FIG. 10c. FIG. 10c shows that the plastically deformable body did not react by ripping, instead, the plastically deformable body does not move as a single unit and a portion of the plastically deformable body, 60, remains on the surface, 55.

Figure 9:
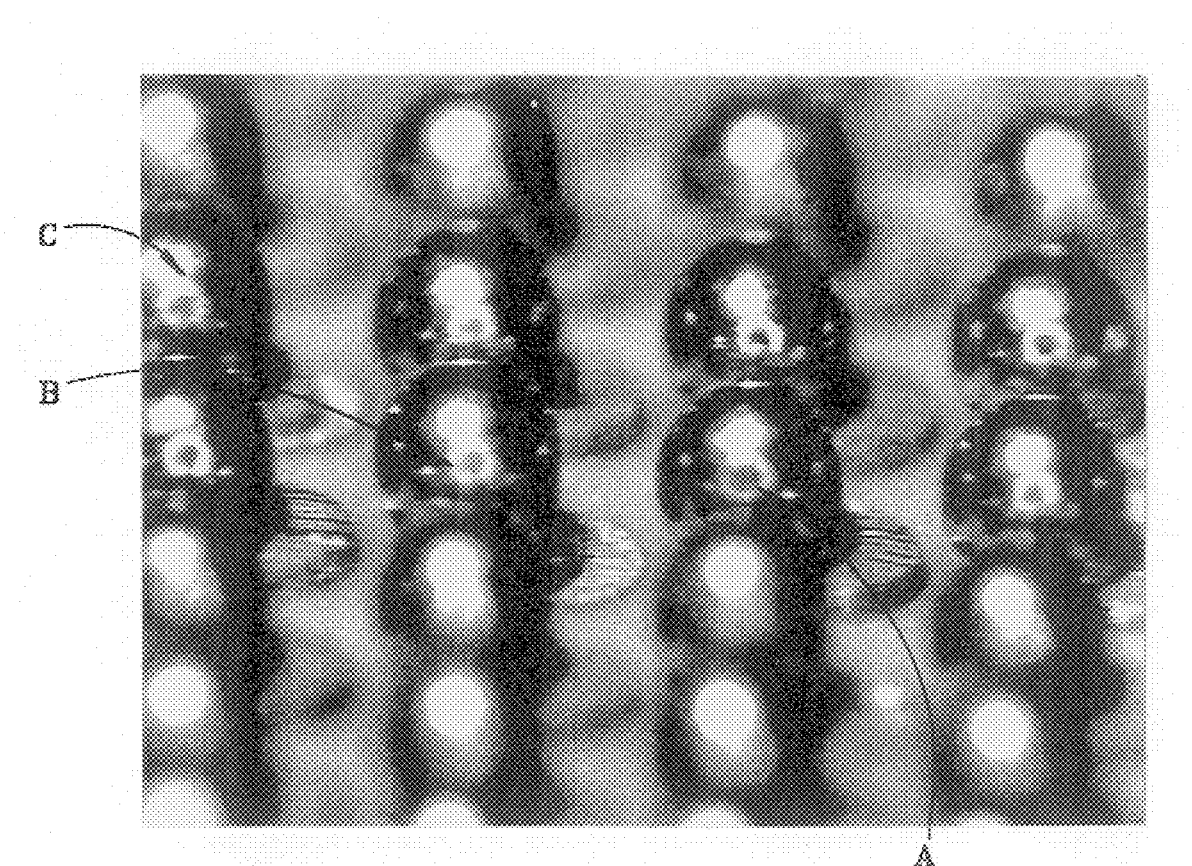
FIG. 9 is a top down view of test objects that have undergone the method of the present invention.

In a preferred embodiment the test objects would be solder balls that have been soldered to the surface. In a preferred embodiment, for any type of plastically deformable body where the reaction to the testing method of the present invention does not conform to a predetermined optimal reaction can be considered as failing the test. An example of an optimal reaction of an operable body for a particular plastically deformable body—surface relationship is shown in A of FIG. 9, where the plastically deformable bodies are solder balls and the surface is ceramic. Examples of reactions not resembling A of FIG. 9 include B and C of FIG. 9. B and C in FIG. 9 shows a plastically deformable body where the movement did not expose a single surface substantially parallel to the surface having the plastically deformable bodies. B and C of FIG. 9 are not the only examples of test reactions that deviate from that shown in A of FIG. 9.

Figure 8A:
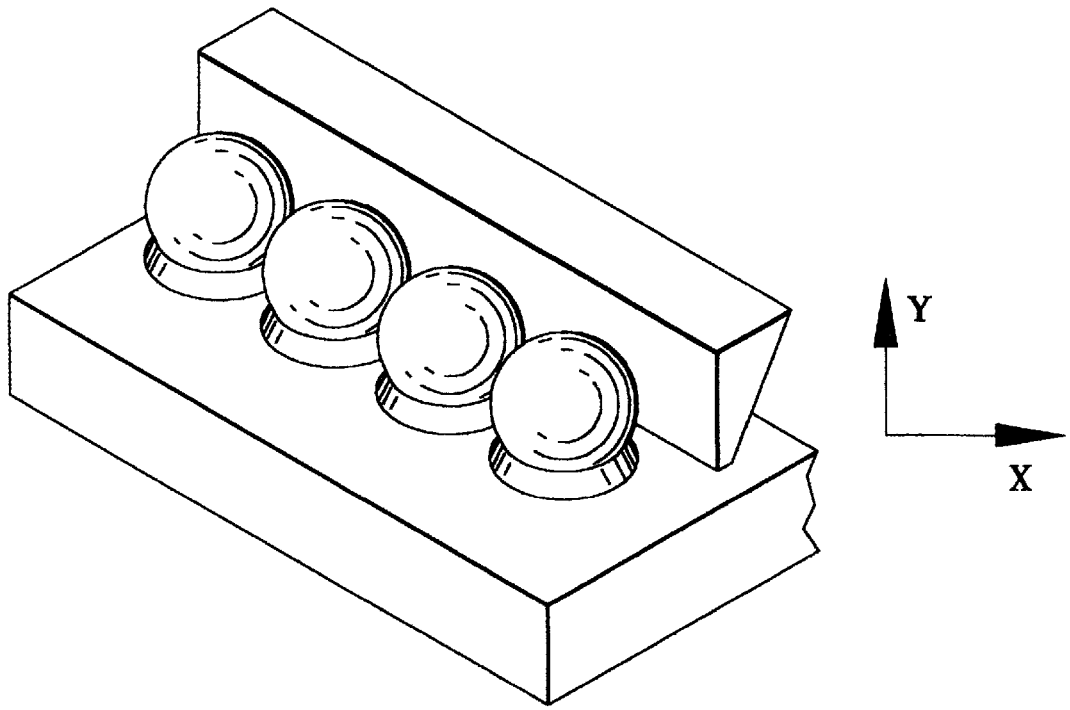
FIGS. 8a and 8b are isometric representations of the method of the present invention.
Figure 8B:
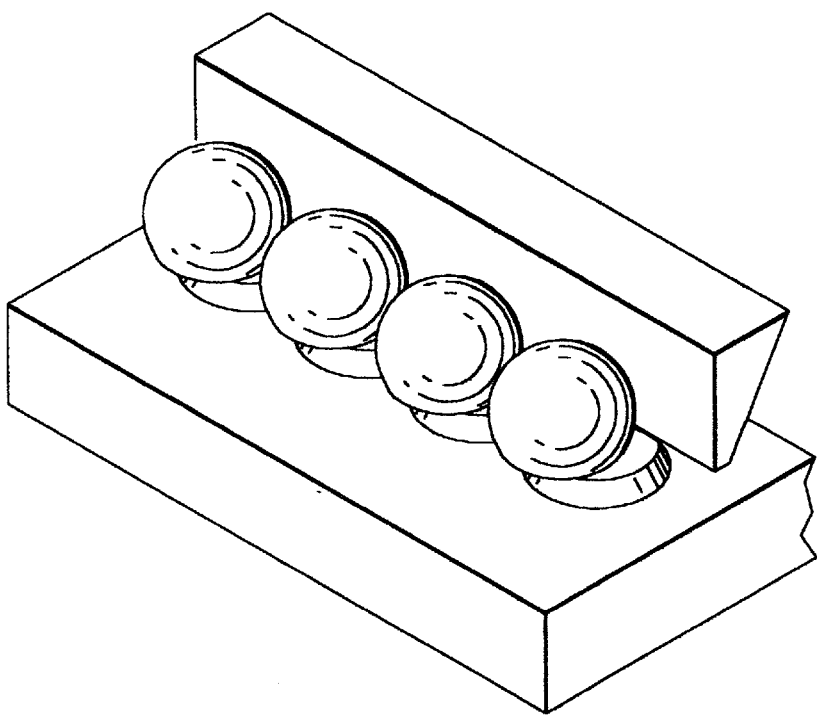
Figure 11:
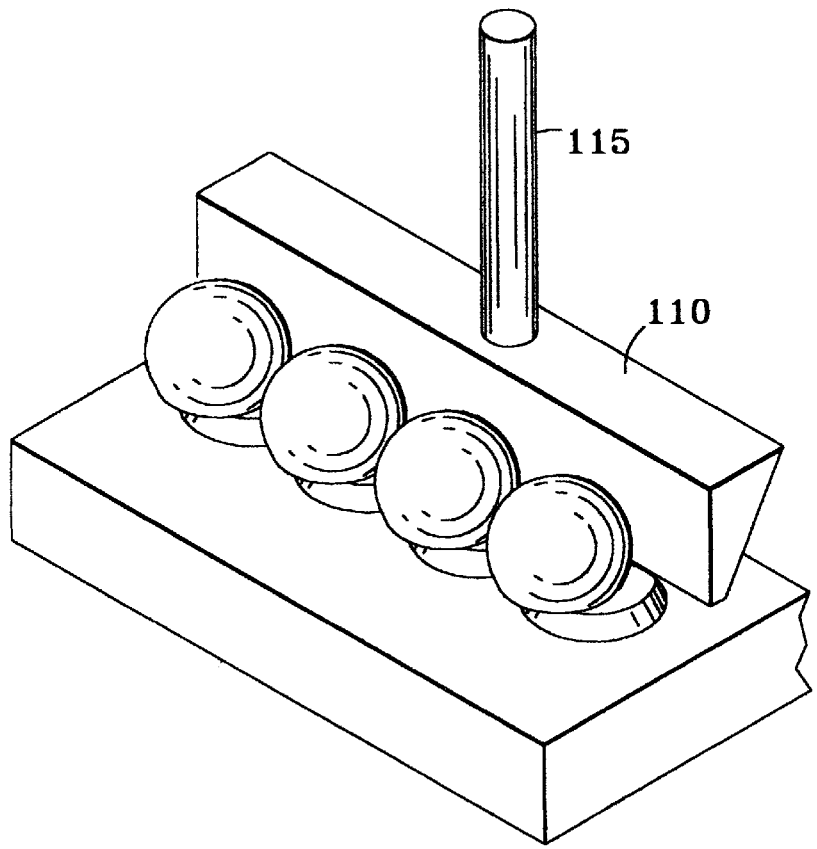
FIG. 11 is yet another cross-sectional view of the method of the present invention.

The method of the invention is shown in FIGS. 8a and 8b. At the first point in time, as shown in FIG. 8a, the moving means, 8, is positioned such that it does not exert significant pressure on the test objects, 5, but is capable of contacting the test objects, 5. At the second point in time, FIG. 8b, the moving means, 8, has contacted the test object, 5, and at least a portion of the test object has shifted due to a force exerted on either the moving means or the surface; the force creating a secondary force between the moving means and the surface. The test objects are then inspected and evaluated for their conformance to the optimal reaction to the interaction of the moving means and the surface. In a preferred embodiment the inspection would be optical and the evaluation would require that 100% of the test objects conform with the optimal reaction. In a preferred embodiment, the force is exerted along a plane parallel to K of FIGS. 10a and 10b. In a more preferred embodiment, the force would be exerted on the moving means. In an even more preferred embodiment, the moving means would have a mover arm capable of imparting the force to the moving means. In an even further more preferred embodiment the mover arm, 115, would be located on the side opposite the side of the moving means facing the surface containing the test objects, 110, as shown in FIG. 11.

It should be noted that the amount of force exerted is not necessarily a measured parameter in the method of the present invention. The amount of force exerted must be great enough to cause the contact of the moving means and the test objects and also great enough to cause the movement of the test objects during the test interval. The method of the present invention is operable when the minimum amount of force necessary for movement of the test objects during the test interval is exerted. Additionally, in a preferred embodiment the force would not be great enough to completely separate the lower portion, 105, and the upper portion 100, as shown in FIG. 10b; this can be accomplished by limiting the travel of the moving means and surface.

In a preferred embodiment of the testing interval involving plastically deformable bodies on a ceramic containing surface, the exposed surface, M, of FIG. 10b, will equal at least about 10% of the diameter, d, of FIG. 4. In a more preferred embodiment of the testing interval involving plastically deformable bodies, the exposed surface, M, will equal at least about 30% of the diameter, d. It would be obvious to one skilled in the art that the larger the exposed area, M, the higher the confidence that a reaction equivalent to an optimal reaction denotes an operable plastically deformable body.

Figure 12:
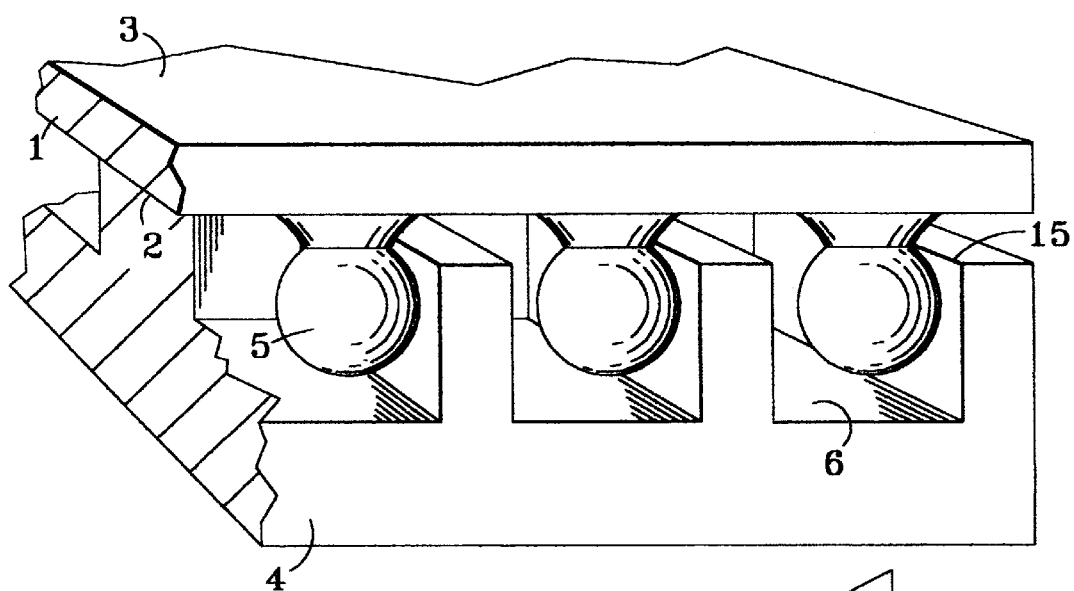
FIG. 12 is another view of the alternative apparatus of the present invention.
Figure 13:
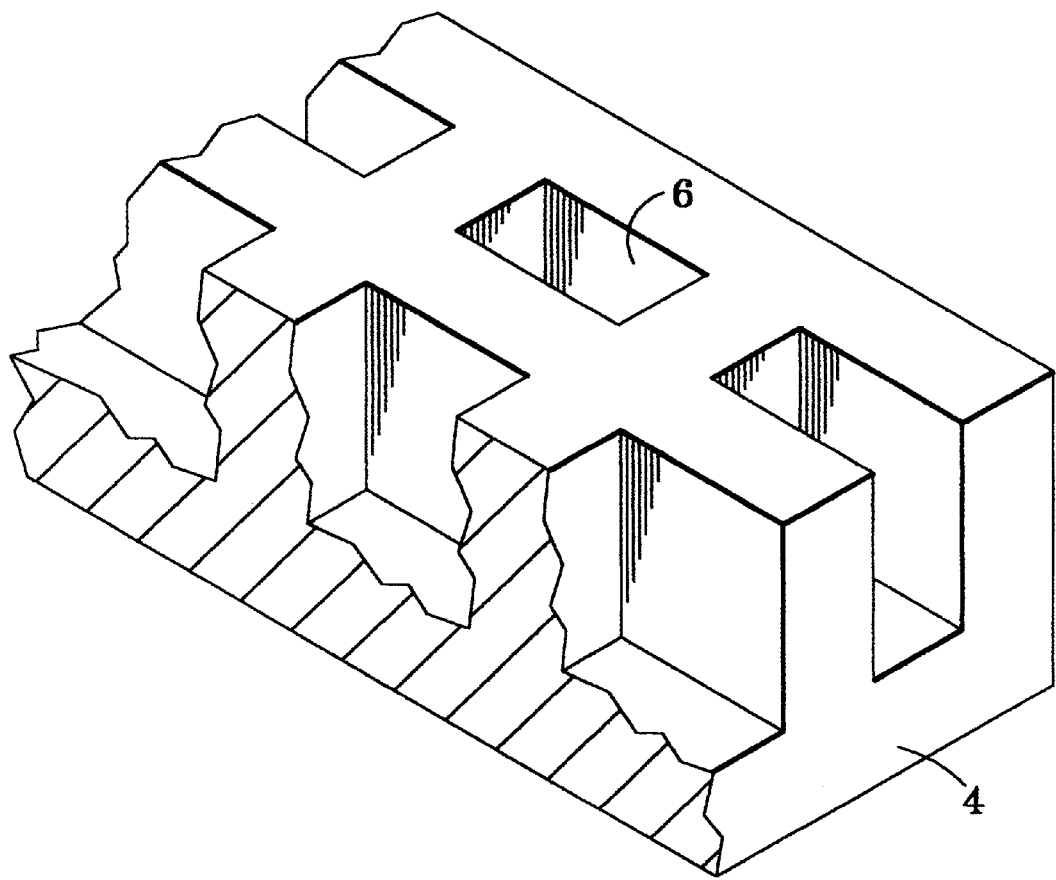
FIG. 13 is yet another view of an alternative apparatus of the present invention.

In an alternative embodiment of the apparatus, as shown in FIG. 12, the moving means, 4, interacts with a surface, 1, containing the test objects, 5, having a top side, 2, and a bottom side, 3. The test objects, 5, are located on the top side, 2, of the surface, 1. The surface, 1, containing the test objects, 5, is inverted so that the bottom side, 3, is over the top side, 2, and inserted into a holder, 4. In this embodiment, the holder, 4, is part of the moving means and must meet the requirements for a shaped object identified earlier. A cross-sectional view of the holder is shown in FIG. 12, where the test object, 5, is held within the holder, 4, such that the lowest effective edge, 15, of the holder, 4, is within the parameters described for a moving means infra. Additionally, the holder would not exert significant pressure on the test objects when the surface is inserted into the holder. When the apparatus is configured in this manner, any plastically deformable bodies that are separated from the surface, after the application of force as described by the arrow, would be retained in the holder and identifying location where potential non-conformities occurred would be facilitated. In a preferred embodiment, shown in FIG. 13, the holder, 4, is configured such that each test object may fit into an individual pocket, 6, of the holder. These pockets could be of any shape, preferably the pockets would be cylindrical or rectangular. In a preferred embodiment, the pockets would retaining any non-conforming test objects that were separated from the surface.

In a method of the alternative embodiment, during the testing interval, the holder is moved between a first position where the test objects, in a first position, are held within the holder without the holder exerting a significant pressure and a second position where a pressure is exerted on the holder such that the lowest effective edge has contacted the test objects and at least a portion of each test object has moved from the first test object position to a second test object position, as shown by the arrow in FIG. 12. In a preferred embodiment, the movement would be along the X axis as described infra and the holder would then be moved back to the first position.

It should be noted that it is not necessary that the test objects be plastically deformable. A test object that is not plastically deformable that is communication with a surface could be tested by the same method and apparatus of the present invention. In the case of a non plastically deformable test object, reactions signifying a conforming test object could be determined by an operator. Certain types of non plastically deformable test objects will have conforming and non conforming reactions that are substantially similar to the reactions of plastically deformable test objects on polymer surfaces.

While the invention has been described in terms of specific embodiments, it is evident in view of the foregoing description that numerous alternatives, modifications and variations will be apparent to those skilled in the art. Thus, the invention is intended to encompass all such alternatives, modifications and variations which fall within the scope and spirit of the invention and the appended claims.

What is claimed is:

1. A method for testing the integrity of at least two test objects, each object comprising a plastically deformable material capable of reflowing, comprising the steps of:
   a. contacting a moving means with the objects at a first point in time, each of the at least two objects having a base portion and a non-base portion capable of reflowing, the moving means having a shaped portion in communication with the non-base portion at a first position;
   b. shifting at least a portion of the objects to a second position at a second time, subsequent to the first time, wherein at least portion of the non-base portion of the objects were displaced during the interval between the first time and the second time;
   c. evaluating the position of the base portion and the non-base portion of each of the objects after the shifting in step b.

2. The method according to claim 1 wherein the evaluation is optical.

3. The method according to claim 2 wherein the evaluation involves a comparison between the objects and a predetermined standard.

4. The method according to claim 1 wherein the shifting is substantially caused by a force exerted on the moving means.

5. The method according to claim 4 wherein the force exerted is the minimal force necessary to cause shifting of the objects.

6. The method according to claim 4 further comprising a mover arm in contact with the moving means, and wherein the force exerted on the moving means is exerted primarily on the moving arm.

7. The method according to claim 1 wherein the objects have a diameter, d, and the objects have a first end and a second end, the objects in contact with a surface on the first end.

8. The method according to claim 7 wherein the diameter of the objects is measured at the surface.

9. The method according to claim 8 wherein the shifting is substantially caused by a force exerted on the moving means.

10. The method according to claim 9 wherein the force is sufficient to shift the objects at least about 10% of the diameter.

11. The method according to claim 10 wherein the force is sufficient to shift the objects at least about 30% of the diameter.

12. The method according to claim 10 wherein the force exerted is less than the shear strength.

13. The method according to claim 8 wherein the moving means has a lowest effective edge.

14. The method according to claim 13 wherein the distance between the surface and the lowest effective edge is at least about 1% and at most about 50% of the diameter prior to the shifting.

15. The method according to claim 14 wherein the distance between the surface and the lowest effective edge is at least about 5% and at most about 30% of the diameter prior to the shifting.

16. The method according to claim 15 further comprising a mover arm in contact with the moving means.

17. The method according to claim 16 wherein the mover arm is positioned opposite the lowest effective edge.

18. An apparatus for testing the integrity of at least two test objects, each object comprising a plastically deformable material capable of reflowing and each object having a base portion and a non-base portion and wherein the each of the base portion of the objects is in communication with a surface, comprising:
   a moving means capable of moving between a first position and a second position, the moving means capable of contacting at least two objects, each object having a base and a non-base portion, the non-base portion capable of reflowing, the base and non-base portions integral to each other in the first position, such that the non-base portions of the objects are capable of being moved between a first position relative to the moving means first position to a second position relative to the moving means second position.

19. The apparatus according to claim 18 further comprising a mover arm in contact with the moving means.

20. The apparatus according to claim 19 wherein the mover arm is in contact with the second end of the moving means.

21. The apparatus according to claim 18 further comprising a distancing portion.

22. The apparatus according to claim 21 wherein the moving means has a lowest effective edge.

23. The apparatus according to claim 22 wherein the distancing portion is positioned between the lowest effective edge and the surface.

24. The apparatus according to claim 18 wherein the objects have a diameter, d, and the objects have a first end and a second end, the objects in contact with a surface on the first end.

25. The apparatus according to claim 24 wherein the diameter of the objects is measured at the surface.

26. The apparatus according to claim 25 wherein the portion of the distancing portion positioned between the lowest effective edge and the surface is at least about 1% and at most about 50% of the diameter of the test objects.

27. The apparatus according to claim 26 wherein the portion of the distancing portion positioned between the lowest effective edge and the surface is at least about 5% and at most about 30% of the diameter of the test objects.

28. An apparatus for testing the integrity of at least two rows of test objects, each object in each row of objects comprising a plastically deformable material capable of reflowing and each object in each row having base portion and a non-base portion and wherein the each of the base portion of the objects is in communication with a surface, comprising:

a moving means assembly having at least a first and a second end, capable of moving between a first position and a second position, the moving means capable of contacting at least two objects, each object having a base and a non-base portion, the non-base portion capable of reflowing, the base and non-base portions integral to each other in the first position, such that the non-base portions of the rows of objects are capable of being moved between a first position relative to the assembly first position to a second position relative to the assembly second position.

29. The apparatus according to claim 28 further comprising a mover arm in contact with the moving means.

30. the apparatus according to claim 29 wherein the mover arm is in contact with the second end of the moving means.

31. The apparatus according to claim 28 further comprising a distancing portion.

32. The apparatus according to claim 31 wherein the moving means has a lowest effective edge.

33. The apparatus according to claim 32 wherein the distancing portion is positioned between the lowest effective edge and the surface.

34. The apparatus according to claim 28 wherein the objects have a diameter, d, and the objects have a first end and a second end, the objects in contact with a surface on the first end.

35. The apparatus according to claim 34 wherein the diameter of the objects is measured at the surface.

36. The apparatus according to claim 35 wherein the portion of the distancing portion positioned between the lowest effective edge and the surface is at least about 1% and at most about 50% of the diameter of the test objects.

37. The apparatus according to claim 36 wherein the portion of the distancing portion positioned between the lowest effective edge and the surface is at least about 5% and at most about 30% of the diameter of the test objects.

* * * * *